US009375286B2

(12) United States Patent
Jung

(10) Patent No.: US 9,375,286 B2
(45) Date of Patent: Jun. 28, 2016

(54) PELVIC STRUCTURE FOR PHYSICAL THERAPY DEVICE AND HEAD FASTENER FOR CERVICAL TRACTION

(76) Inventor: Won-ha Jung, Guri-si (KR)

(*) Notice: Subject to any disclaimer, the term of this patent is extended or adjusted under 35 U.S.C. 154(b) by 561 days.

(21) Appl. No.: 13/806,416

(22) PCT Filed: Jun. 15, 2011

(86) PCT No.: PCT/KR2011/004371
§ 371 (c)(1),
(2), (4) Date: Mar. 4, 2013

(87) PCT Pub. No.: WO2011/162503
PCT Pub. Date: Dec. 29, 2011

(65) Prior Publication Data
US 2013/0218062 A1    Aug. 22, 2013

(30) Foreign Application Priority Data

Jun. 23, 2010 (KR) .................. 10-2010-0059357

(51) Int. Cl.
*A61F 5/00* (2006.01)
*A61B 19/00* (2006.01)
*A61H 1/02* (2006.01)

(52) U.S. Cl.
CPC .............. *A61B 19/26* (2013.01); *A61H 1/0218* (2013.01); *A61H 1/0222* (2013.01); *A61H 2201/163* (2013.01); *A61H 2201/1607* (2013.01); *A61H 2203/0456* (2013.01); *A61H 2205/081* (2013.01)

(58) Field of Classification Search
CPC .............. A61B 19/26; A61B 17/3403; A61B 2017/3411; A61B 2019/5251; A61B 2019/5255; A61B 5/0555; A61B 5/702; A61B 5/1076; A61B 5/4504; A61H 1/0218; A61H 1/0222; A61H 2201/1607; A61H 2201/163; A61F 5/0585; A61F 5/34; A61F 2005/0153; A61F 5/05816; A61F 5/05841; A61F 5/32; A61F 5/028; A61F 5/0193; A61F 5/055; A61F 5/058; A61F 13/0273; A61F 13/062; A61F 5/05833; A61F 5/0588; A61F 5/0102; A61F 2/36; A61F 2/4609; A61F 2002/2835; A61F 2002/30009; A61F 2002/30014; A61F 2002/30062; A61F 2002/3007; A61F 2002/30133; A61F 2002/30136; A61F 2002/4632; A61F 2/4657; A61F 2002/4668; A61F 2/34; A61F 2002/30163; A61F 2002/30166; A61F 2002/30172; A61F 2002/30181; A61F 2002/30401; A61F 2002/30507
USPC ........... 5/59, 30, 47, 602, 648, 649, 650, 651; 602/32–39; 128/845, 869–870
See application file for complete search history.

(56) References Cited

U.S. PATENT DOCUMENTS 3,228,399 A * 1/1966 Riedell .................. A61B 17/42
128/845
3,873,081 A * 3/1975 Smith .................... A61G 13/12
5/621

(Continued)

FOREIGN PATENT DOCUMENTS

KR           100711104 B1    4/2007
KR      1020090029044 A     3/2009

*Primary Examiner* — Michael Brown
(74) *Attorney, Agent, or Firm* — STIP Law Group, LLC

(57) ABSTRACT

The present invention concerns a pelvic fastener for lumbar traction of physical therapy device and head fastener for cervical traction, which supports a pelvis in a comfortable and firm manner, maintains a predetermined level of traction intensity without being detached or slid down, maximizes a treatment effect by concentrating a traction force on the lumbar and preventing power dispersion, is intended for patient treatment or correction by means of cervical traction, and does not pressurize a patient's head or function in an unstable manner. For a traction therapy device comprising a bed plate (2) disposed at an upper portion of a frame (1) such that the bed plate (2) may move backwards and forwards and a pelvic bed (3) attached to an upper portion of the bed plate (2) to support the lumbar, the pelvic support structure of the present invention comprises: brackets (10) connected by means of shafts (H1) to both front sides of the bed plate (2) in a rotatable manner; pelvic supporters (20) connected by means of shafts (H2) to upper portions of the brackets (10) in a rotatable manner and having a curved shape to surround a pelvis; pelvic cushions (30) disposed at inner surfaces of the pelvic supporters (20) to come into tight contact with the pelvis; and female and male buckles (40 and 50) connected to upper portions of the pelvic supporters (20) and the pelvic cushions (30) by means of bands (41 and 51), the female and male buckles (40 and 50) being one-touch detachable type.

4 Claims, 6 Drawing Sheets

(56) References Cited

U.S. PATENT DOCUMENTS

| | | | |
|---|---|---|---|
| 4,911,179 A | 3/1990 | Brown et al. | |
| 5,060,327 A * | 10/1991 | Celestina | A61G 13/0009 297/183.9 |
| 5,479,666 A * | 1/1996 | Foster | A61G 7/002 297/423.3 |
| 2001/0047142 A1 | 11/2001 | Manoach | |
| 2003/0088919 A1 | 5/2003 | Lin | |
| 2003/0139777 A1 | 7/2003 | Xiao et al. | |
| 2005/0010152 A1 | 1/2005 | Becerra et al. | |

* cited by examiner

PELVIC STRUCTURE FOR PHYSICAL THERAPY DEVICE AND HEAD FASTENER FOR CERVICAL TRACTION

CROSS-REFERENCE TO RELATED APPLICATION

This application claims the benefit of Korean Patent Application No. 10-2010-0059357, filed on Jun. 23, 2010 in the Korean Intellectual Property Office, the disclosure of which is incorporated herein by reference.

TECHNICAL FIELD

The present invention relates to a pelvic fastener for lumbar traction of physical therapy device and head fastener for cervical traction, and more particularly, to a pelvic support structure for a physical therapy device and a head fastener for cervical traction, which supports a pelvis in a comfortable and firm manner, maintains a predetermined level of traction intensity without being detached or slid down, maximizes a treatment effect by concentrating traction force on the lumbar vertebrae and preventing power dispersion, is intended for patient treatment or correction by means of cervical traction, and does not pressurize a patient's head or function in an unstable manner, in a physical treatment.

TECHNICAL FIELD

Generally, a physical therapy device is to treat and correct a pain of a diseased condition occurring in a skeletal system, an arthrometer, a muscles system and a nervous system or the like of a human body by using a drop and a traction, and various types of physical therapy device for medicinal purposes are provided.

In the physical therapy devices, to treat and correct a pain of a diseased condition, such as a lumbar disc, disc stenosis, chronic back pain, sciatic neuralgia, a nervous disease with lumbar malposition, or the like, which occur in the region of a lumbar vertebrae of a body by using a traction, the lumbar vertebrae has to be supported in a comfortable and firm manner.

However, in the related arte, a pelvis is supported by only using a belt, and thus, a pelvis cannot be supported in a comfortable and firm manner structurally in a physical treatment. Also, a predetermined level of traction intensity cannot be maintained because of a belt being detached or slid down. Therefore, power is dispersed, and traction force cannot be concentrated on a region of a lumbar vertebrae, and thus, a treatment effect is insufficient.

A traction treatment is operated in a physical therapy device or an apparatus (including an automatic or hand-operated physical therapy device and apparatus or the like) raising cervical vertebrae (a neck) for a treatment or a correction, when a chin of a patient is being generally taken by a harness (a chin belt), and thus, a neck is being raised, or when a back end of a neck of a patient is being taken by using a rubber-material pad hung on occipital bone (a back end of a neck) of a lying patient, and thus, a forehead is being fixed by using a headband.

However, when the harness is used, there are an inconvenient due to a pressure to a region of a chin of a patient during a traction of cervical vertebrae, and uncertainty about a treatment efficiency.

Also, the related art device for fixing a head only fixes a head, and fixes and presses a region of a forehead such that a head is not moved. Therefore, users and patients have aversion about using the device, and the device causes a headache.

DISCLOSURE OF INVENTION

Accordingly, the present invention is directed to provide a pelvic fastener for lumbar traction of physical therapy device and head fastener for cervical traction, which substantially obviates one or more problems due to limitations and disadvantages of the related art. An aspect of the present invention is directed to provide a pelvic support structure for physical therapy device and a head fastener for cervical traction, which supports a pelvis in a more comfortable and firm manner in a traction treatment for a region of lumbar vertebrae, maintains a predetermined level of traction intensity without being detached or slid down in a physical treatment for a region of lumbar vertebrae, maximizes a treatment effect by concentrating traction force on the lumbar vertebrae and preventing power dispersion in a traction treatment for a region of lumbar vertebrae, and is used in medical devices or apparatuses raising cervical vertebrae (a neck) to solve problems, such as inconveniences which occur when the devices or the apparatuses are used for a treatment or a correction, side effects which occur because a head is not exactingly fixed when the devices or the apparatuses are used, or the like.

To achieve these and other advantage and in accordance with the purpose of the invention, as embodied and broadly described herein, there is provided a pelvic fastener for lumbar traction of physical therapy device, which includes: brackets respectively connected by each of shafts to both front sides of the bed plat rotatably in a left-and right direction; pelvic supporters respectively connected by each of shafts to upper portions of the brackets rotatably in a left-and-right direction, having a curved shape to surround a pelvis and formed of metal material; pelvic cushions respectively disposed at inner surfaces of the pelvic supporters to come into tight contact with the pelvis; and female and male buckles connected to upper portions of the pelvic supporters and the pelvic cushions by means of bands, the female and male buckles being one-touch detachable type.

To achieve these and other advantage and in accordance with the purpose of the invention, as embodied and broadly described herein, there is provided a head fastener for cervical traction, which uses a fixing method the same as the related art method fixing a back end of a neck of a patient, that is, occipital bone with a pad, couples a chin-belt fixing apparatus to a bunch of cervical vertebrae pads to disperse traction force to a pad, a front chin belt or the like, in a traction treatment, and minimizes situation in which force is concentrated to a special region, and thus, enables a stable and convenient traction treatment to be performed.

To achieve these and other advantage and in accordance with the purpose of the invention, as embodied and broadly described herein, there is provided a head fastener for cervical traction for medicinal purposes, which includes a head support 200 formed to support a head of a person receiving treatment. Here, the head support comprises: a neck fixing part holding a neck through an upper portion, which supports a head, is formed to open and close an upper part, and is opened, a left chin support and a right chin support are formed to fix a chin in a periphery of the neck fixing part, a control box, in which the left chin support and the right chin support are coupled to a gap control screw such that a gap between the left chin support and the right chin support is controlled by a gap control lever, and left and right chin supporting pad fixing parts couple to an upper portion of the left and right chin supports to fix a chin supporting pad.

Advantageous Effects

According to the pelvic fastener for lumbar traction of physical therapy device of the present invention, the pelvic support structure can support a pelvis in a more comfortable and firm manner structurally in a traction treatment for a region of lumbar vertebrae, and can doubly support a pelvis without being detached or slid down in a traction treatment for a region of lumbar vertebrae more stably and efficiently to maintain a predetermined level of traction intensity. Therefore, the pelvic support structure can prevent power from being disperse, concentrate traction force on the lumbar vertebrae to maximize a treatment effect in a traction treatment. Moreover, according to the head fastener for cervical traction for medicinal purposes used in a treatment, a correction or the like, a head can be comfortably fixed, and can be safely fixed without causing aversion to a user or a patient.

BRIEF DESCRIPTION OF DRAWINGS

The accompanying drawings, which are included to provide a further understanding of the invention and are incorporated in and constitute a part of this application, illustrate embodiments of the invention and together with the description serve to explain the principle of the invention. In the drawings:

FIGS. 1 to 6a and 6b are exemplary diagrams illustrating a pelvic fastener for lumbar traction according to an embodiment of the present invention, and FIG. 1 is a perspective view illustrating an installation state of the present invention;

FIG. 2 is a perspective view of the present invention;

FIG. 3 is an enlarged sectional view of a portion "A" of FIG. 2;

FIG. 4 is a perspective view illustrating a main part of the present invention;

FIG. 5 is an exploded perspective view of FIG. 4; and

FIGS. 6a and 6b are exemplary diagrams illustrating an operation of the present invention, FIG. 7 is a perspective view illustrating a head fastener for cervical traction for medicinal purposes according to an embodiment of the present invention;

FIG. 8 is a perspective view illustrating the head fastener for cervical traction for medicinal purposes according to the present invention with a chin supporting pad;

FIG. 9 is a perspective view illustrating another head supporting part applied to the present invention; and FIG. 10 is an exemplary diagram illustrating a using state of the present invention.

Figure 1:
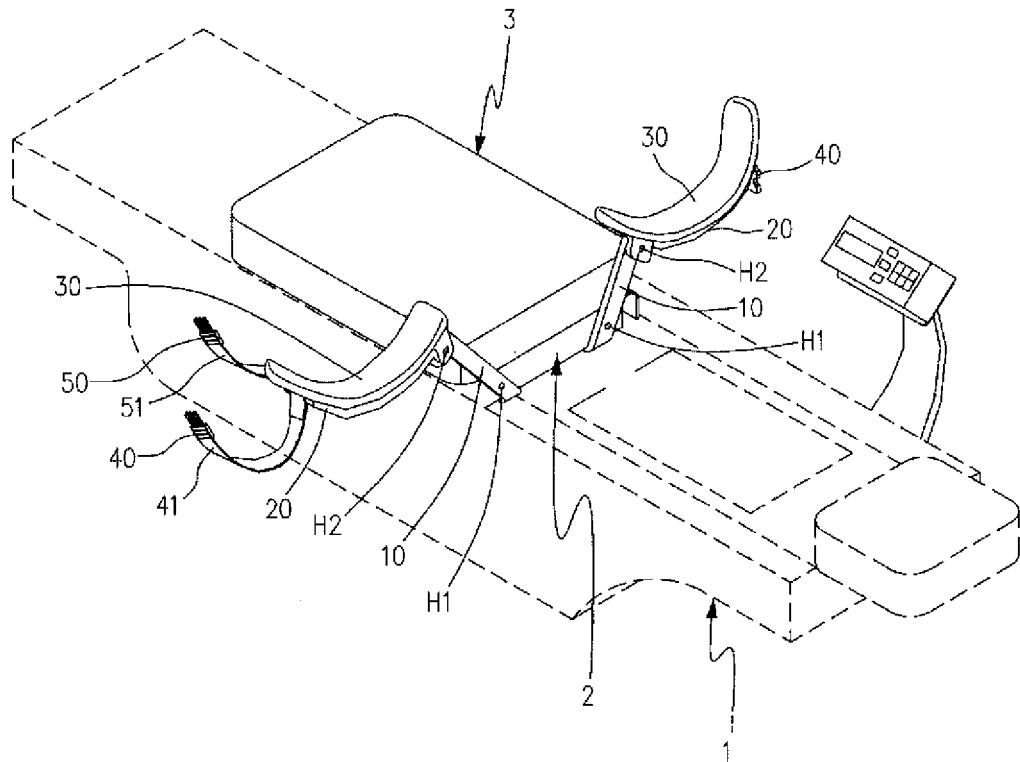

| Descriptions of reference numbers | |
|---|---|
| 1: frame | 2: bed plate |
| 2a: supporting board | 3: pelvic bed |
| 10: bracket | 11: connecting piece |
| 12: reinforcing piece | 20: pelvic supporter |
| 21: vertical long hole | 22, 23: horizontal long hole |
| 21a, 22a, 23a: slope inserting hole | 30: pelvic cushion |
| 31, 32: connecting part | 40, 50: buckle |

| Descriptions of reference numbers | |
|---|---|
| 41, 51: band | 41a: connecting part |
| H1, H2, H3: shaft | |
| 100: support | 110: rail |
| 200: head supporting part | 210, 220: left and right support |
| 230: neck fixing part | 240: upper body supporting part |
| 250, 260: left and right chin support | 270: gap control screw |
| 280: gap control lever | 290: left chin supporting pad fixing part |
| 300: fixing bolt | 310: right chin supporting pad fixing part |
| 320: protrusion | 330: front protrusion |
| 340: separation preventing groove | 350: control box |
| 360: rear protrusion | 400: lower body supporting part |
| 410: rotation angle rail groove | 420: stop bolt |
| 440: nut | 450: stopper |
| 460: rotation shaft | |

MODES FOR CARRYING OUT THE INVENTION

Reference will now be made in detail to the exemplary embodiments of the present invention, examples of which are illustrated in the accompanying drawings. Wherever possible, the same reference numbers will be used throughout the drawings to refer to the same or like parts. Hereinafter, a pelvic support structure for physical therapy device and a head fastener for cervical traction according to the embodiments of the present invention will be described in detail with reference to the accompanying drawings.

A pelvic fastener for lumbar traction of physical therapy device applied to a traction therapy device comprising a bed plate 2 disposed at an upper portion of a frame 1 such that the bed plate 2 moves backwards and forwards, and a pelvic bed 3 attached to an upper portion of the bed plate 2 to support lumbar vertebrae, as shown in FIGS. 1 to 6a and 6b, includes brackets 10 respectively connected by each of shafts H1 to both front sides of the bed plate 2 rotatably in a left-and right direction; pelvic supporters 20 respectively connected by each of shafts H2 to upper portions of the brackets 10 rotatably in a left-and-right direction and having a curved shape to surround a pelvis; pelvic cushions 30 respectively disposed at inner surfaces of the pelvic supporters 20 to come into tight contact with the pelvis; and female and male buckles 40 and 50 connected to upper portions of the pelvic supporters 20 and the pelvic cushions 30 by means of bands 41 and 51. Here, the female and male buckles 40 and 50 are one-touch detachable type.

The frame 1 configures a main body of the traction therapy device, and the frame 1 supports the bed plate 2 such that the bed plate 2 moves backwards and forwards.

The bed plate 2 is disposed at an upper portion of the frame 1 such that the bed plate 2 moves backwards and forwards, and the bed plate 2 supports the pelvic bed 3.

The pelvic bed 3 supports is attached to an upper portion of the bed plate 2 to support lumbar vertebrae, and the pelvic bed 3 treats and corrects a pain of a diseased condition occurring in a region of lumbar vertebrae of a human body by using a traction.

Here, the pelvic fastener for lumbar traction of physical therapy device according to the present invention, as described above, includes brackets 10, pelvic supporters 20, pelvic cushions 30 and female and male buckles 40 and 50.

The brackets 10 are respectively connected by each of shafts (H1) to both front sides of the bed plate 2, and the brackets 10 supports each of the pelvic supporters 20 such that each of the pelvic supporters rotates.

Figure 2:
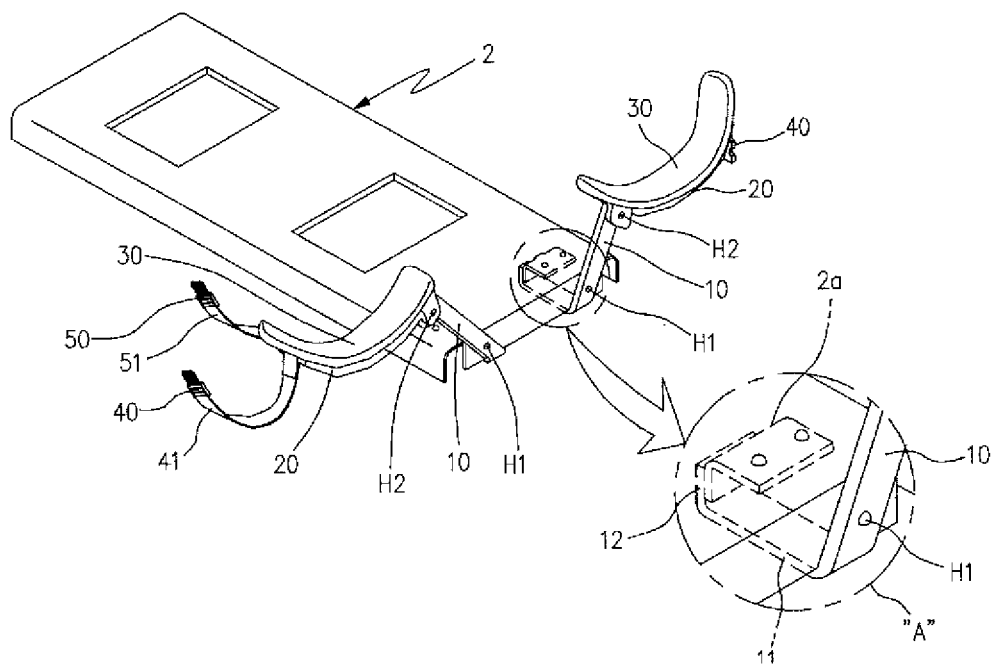
Figure 3:
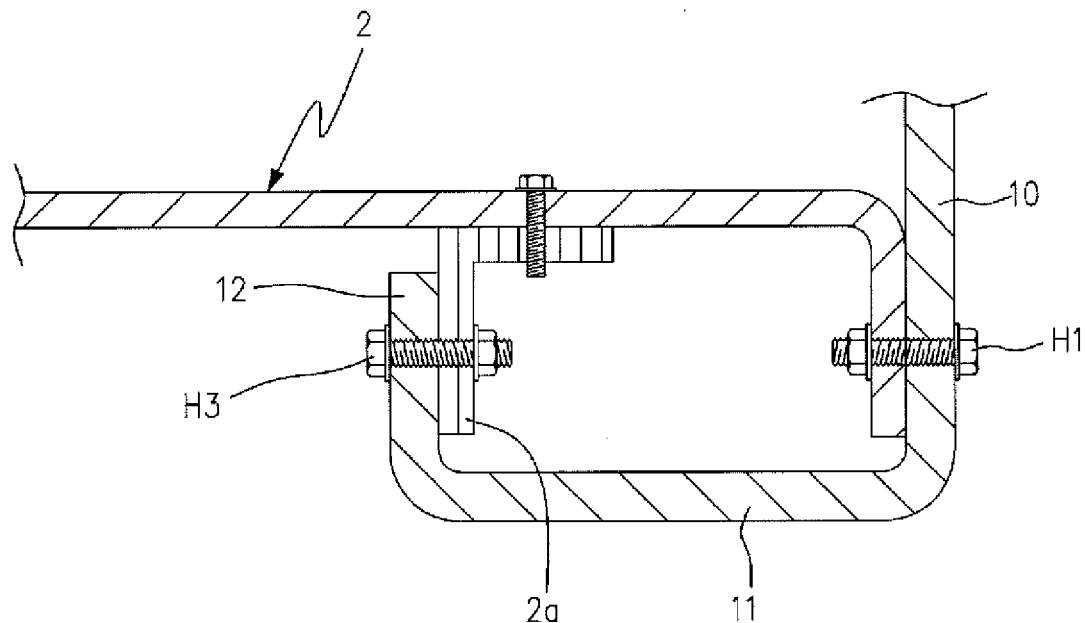

According to the present invention, as shown in FIGS. 2 and 3, supporting boards 2a are respectively disposed at both lower portions of a front side of the bed plate 2, a connecting piece 11 expanding to the supporting board 2a is bent in a horizontal direction to be formed in a lower portion of the bracket 10, and a reinforcing piece 12 connected to the supporting board 2a of the bed plate 2 rotatably in a left-and-right direction by the shaft H3 is bent in a vertical direction to be formed in an end portion of the connecting piece 11.

The pelvic supporters 20 respectively connected by each of shafts H2 to upper portions of the both brackets 10 such that each of the pelvic supporters 20 rotates in a left-and-right direction, and are respectively formed in a curved shape so as to support a pelvis in a comfortable and firm manner.

Figure 4:
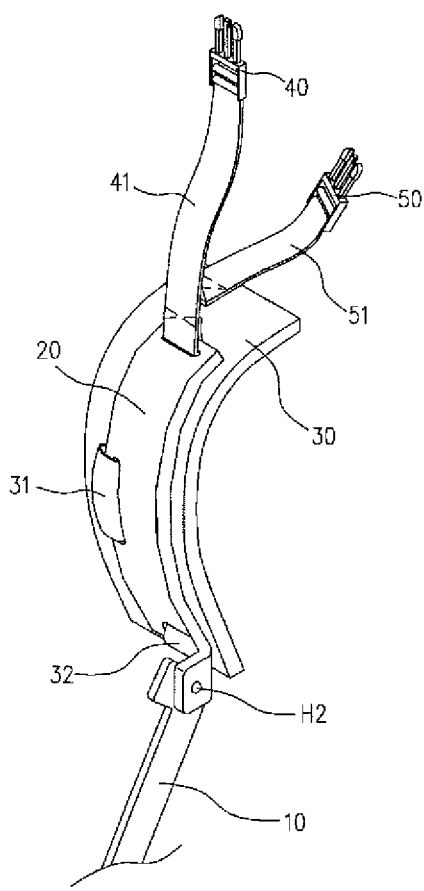
Figure 5:
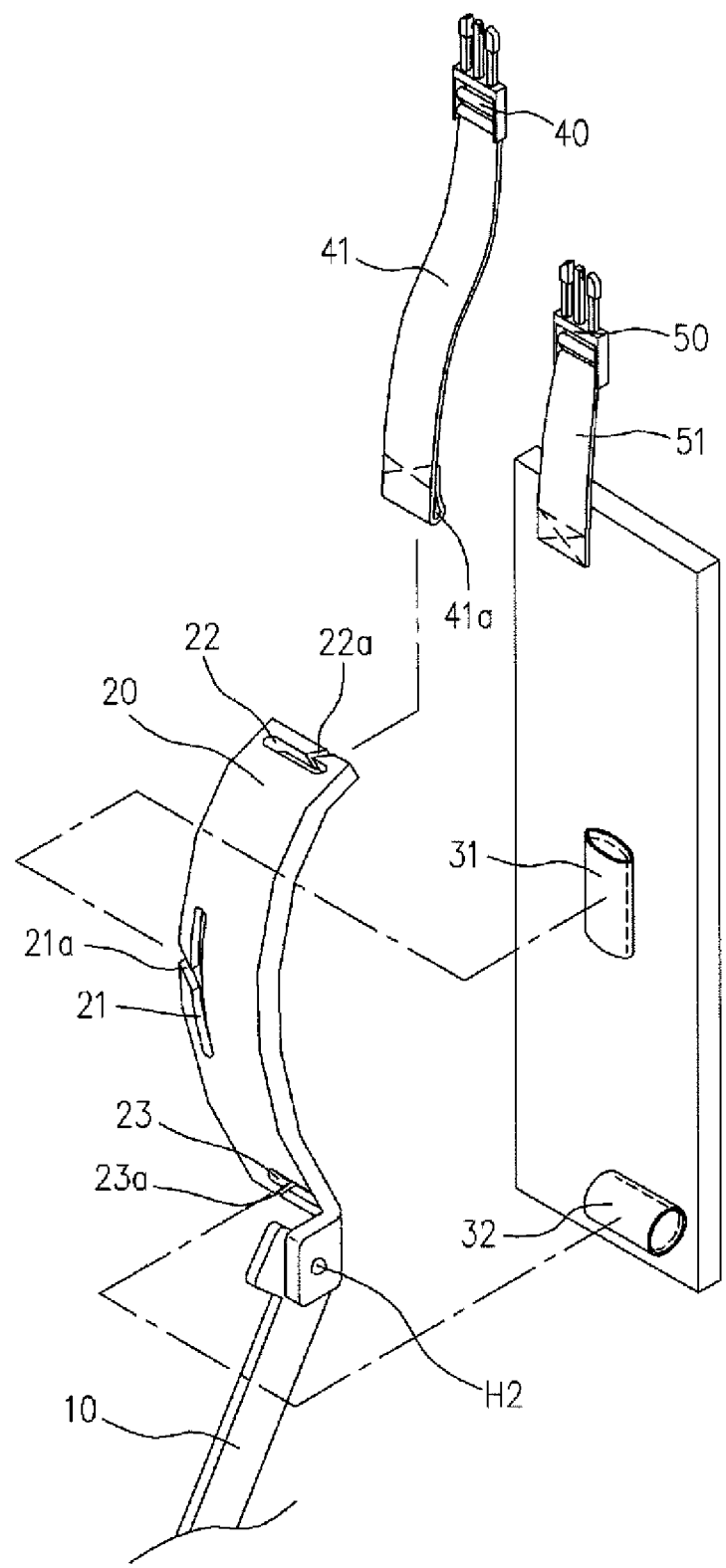

According to the present invention, as shown in FIGS. 4 and 5, a vertical long hole 21 having a slope inserting hole 21a opening into the outside is formed in one side of a central portion of the pelvic supporter 20, and horizontal long holes 22 and 23, each of which has a slope inserting hole 22a or 23a opening into the outside, are respectively formed in an upper portion and a lower portion of the pelvic supporter 20. Here, the pelvic cushion 30 is connected to the vertical long hole 21 and the horizontal long hole 23 of the pelvic supporter 20, and a band 41 is connected to the horizontal long hole 22 of the pelvic supporter 20.

Moreover, according to the present invention, to support the pelvis more stably in a traction treatment, the pelvic supporter 20 is formed of a metal which is not transformed and maintain an original form.

Each of the pelvic cushions 30 is disposed at the inner surface of the pelvic supporter 20 to closely contact the pelvis, and the pelvic cushion 30 supports the pelvis comfortably.

According to the present invention, as shown in FIGS. 4 and 5, each of connecting parts 31 and 32 is attached to the central portion and the lower portion of an outer surface of the pelvic cushion 30. Each of the connecting parts 31 and 32 is inserted into the vertical long hole 21 and the horizontal long hole 23 through the slope inserting holes 21a and 23a of the pelvic supporter 20. Therefore, according to the present invention, the pelvic cushion 30 can be easily coupled to the pelvic supporter 20 by inserting each of the connecting parts 31 and 32 into the vertical long hole 21 and the horizontal long hole 23 through the slope inserting holes 21a and 23a. On the other hands, the pelvic cushion 30 can be easily separated from the pelvic supporter 20 by picking out the connecting parts 31 and 32 inserted into the vertical long hole 21 and the horizontal long hole 23 through the slope inserting holes 21a and 23a. Therefore, in case of need, the pelvic cushion 30 can be easily replaced. At this point, the connecting parts 31 and 32 are attached to the central portion and the lower portion of the outer surface of the pelvic cushion 30 by using a sewing method.

Each of the female and male buckles 40 is connected to the upper portion of the pelvic supporter 20 by means of the band 41, and the female and male buckles 40 are connected to each other with one-touch detachable type.

According to the present invention, as shown in FIGS. 4 and 5, a connecting part 41a inserted into the horizontal long hole 22 through the slope inserting hole 22a of the pelvic supporter 20 is formed in one end portion of the band 41. Therefore, according to the present invention, the band 41 can be easily coupled to the pelvic supporter 20 by inserting the connecting part 41a into the horizontal long hole 22 through the slope inserting hole 22a, and on the other hands, the band 41 can be easily separated from the pelvic supporter 20 by picking out the connecting parts 41 inserted into the horizontal long hole 22 through the slope inserting holes 22a. Therefore, in case of need, the band 41 can be easily replaced.

Each of the female and male buckles 50 is connected to the upper portion of the pelvic cushion 30 formed in each of both sides by means of the band 51, and the female and male buckles 50 are connected to each other with one-touch detachable type.

According to the present invention, one end portion of the band 51 is attached to outer side of the pelvic cushion 30 by using a sewing method.

Figure 6A:
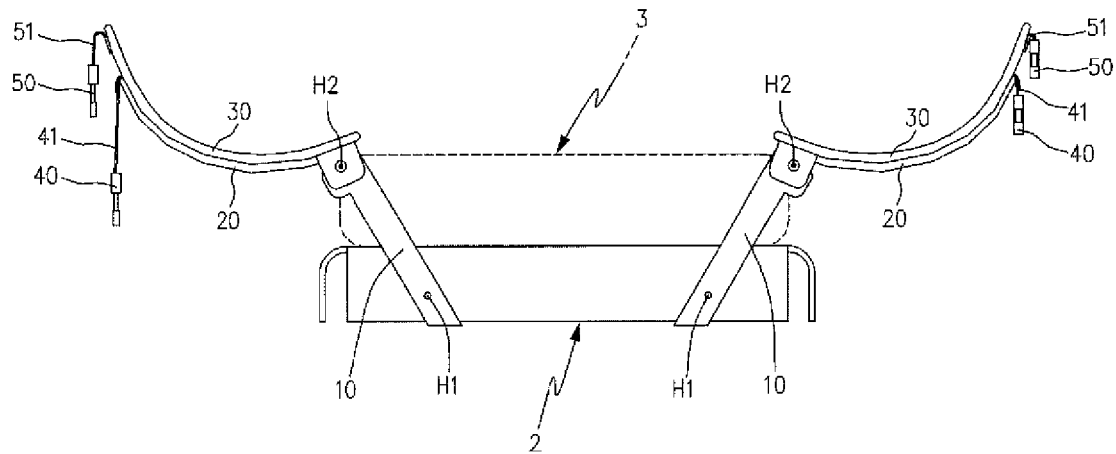
Figure 6B:
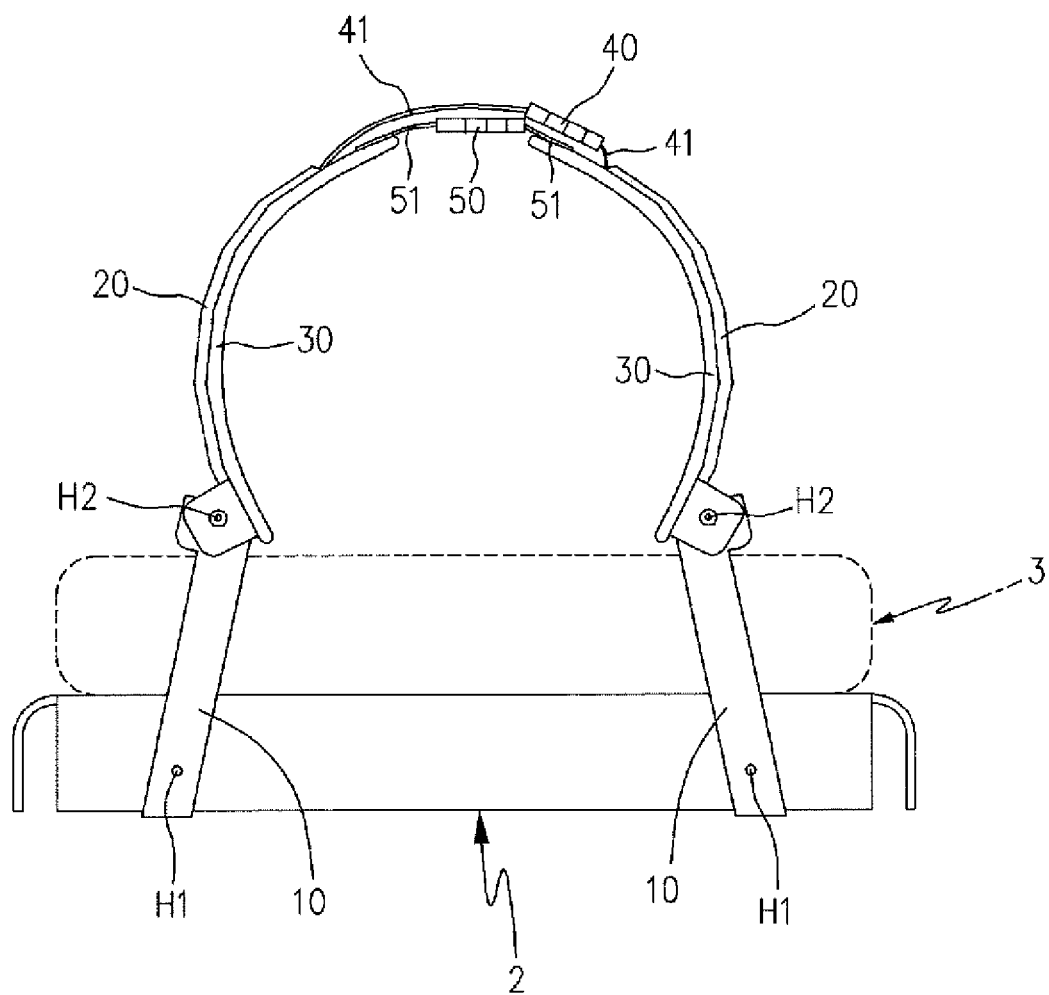

In the pelvic fastener for lumbar traction of physical therapy device according to the present invention, because each of the pelvic supporters 20 surrounding the pelvis to support the pelvis in a traction treatment is formed in a curved shape and formed of metal material, the pelvic support structure can stably support the pelvis structurally. Also, because the pelvic cushion 30 closely contacting the pelvis to provide a cushioned feeling is disposed at the inside of the pelvic supporter 20, the pelvic support structure can comfortably surround the pelvis to support the pelvis structurally. Moreover, as shown in FIG. 6b, if the female and male buckles 40 and 50 respectively connected to the pelvic supporter 20 and the pelvic cushion 30 are coupled when the both of the pelvic supporters 20 are surrounding the pelvis, the pelvis can be doubly and stably supported, and thus, predetermined level of traction intensity can be maintained.

Therefore, according to the present invention, and as described above, because the pelvic supporter 20 formed of metal material and the pelvic cushion 30 providing a cushioned feeling surround the pelvis to support the pelvis, the pelvic can be more comfortably and stably supported structurally in a physical treatment for a region of lumbar vertebrae.

Moreover, according to the present invention, and as described above, because the female and male buckles 40 and 50 of the both sides respectively connected to the pelvic supporter 20 and the pelvic cushion 30 doubly and stably surround the pelvis to comfortably and stably support the pelvis, the pelvis can be more doubly, stably and effectively supported without being detached or slid down structurally in a traction treatment for a region of lumbar vertebrae, and a predetermined level of traction intensity can be maintained. Also, this can prevent power dispersion in a traction treatment for a region of lumbar vertebrae, and maximize a treatment effect by concentrating a traction force on the lumbar vertebrae.

Also, according to the present invention, and as described above, each of the pelvic cushion 30 and the band 41 can be easily coupled to the pelvic supporter 20 by inserting the connecting parts 31, 41a and 32 into the vertical and horizontal long holes 21, 22 and 23 through the slope inserting holes 21a, 22a and 23a, and on the other hands, each of the pelvic cushion 30 and the band 41 can be easily separated from the pelvic supporter 20 by picking out the connecting parts 31, 41a and 32 inserted into the vertical and horizontal long holes 21, 22 and 23 through the slope inserting holes 21a, 22a and 23a. Therefore, in case of need, the pelvic cushion 30 and the band 41 can be easily replaced.

Hereinafter, the head fastener for cervical traction according to the present invention will be described in detail with reference to the accompanying drawings.

An embodiment of the present invention will be described in detail with reference to the accompanying drawing.

It will be apparent to those skilled in the art that various modifications and variations can be made in the present invention without depart ing from the spirit or scope of the inventions. Thus, it is intended that the present invention covers the modifications and variations of this invention provided they come within the scope of the appended claims and their equivalents. Here, reference will now be made in detail to the exemplary embodiments of the present invention, examples of which are illustrated in the accompanying drawings. Wherever possible, the same reference numbers will be used throughout the drawings to refer to the same or like parts.

The head fastener for cervical traction according to the present invention, as shown in FIGS. 7 to 10, includes a support 100 including rails 110 formed in both sides, a head supporting part 200 disposed at a head portion of the support 100, an upper body supporting part 240 disposed at an upper body portion of the support 100, a lower body supporting part 400 disposed at a lower body portion of the support 100, a connecting means 500 formed to connect or separate the upper body supporting part 240 and the lower body supporting part 400, and a pressure means 600 formed to push or pull when the pressure means 600 is being connected to the lower body supporting part 400.

Figure 7:
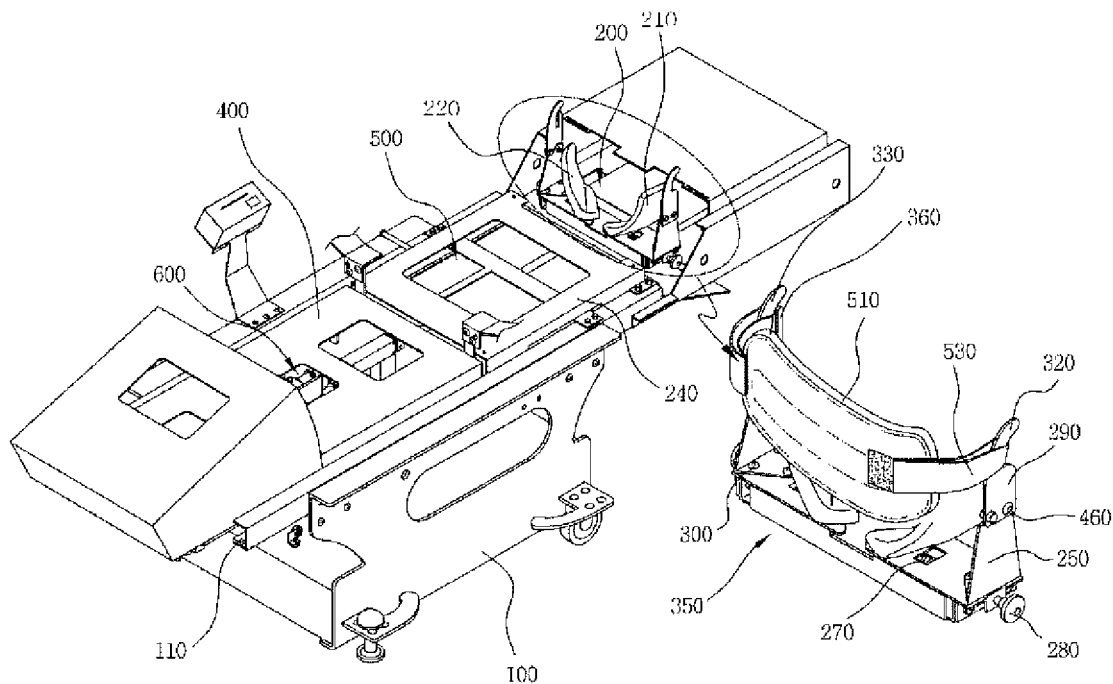
FIGS. 7 to 10 are exemplary diagrams illustrating a head fastener according to an embodiment of the present invention.
Figure 8:
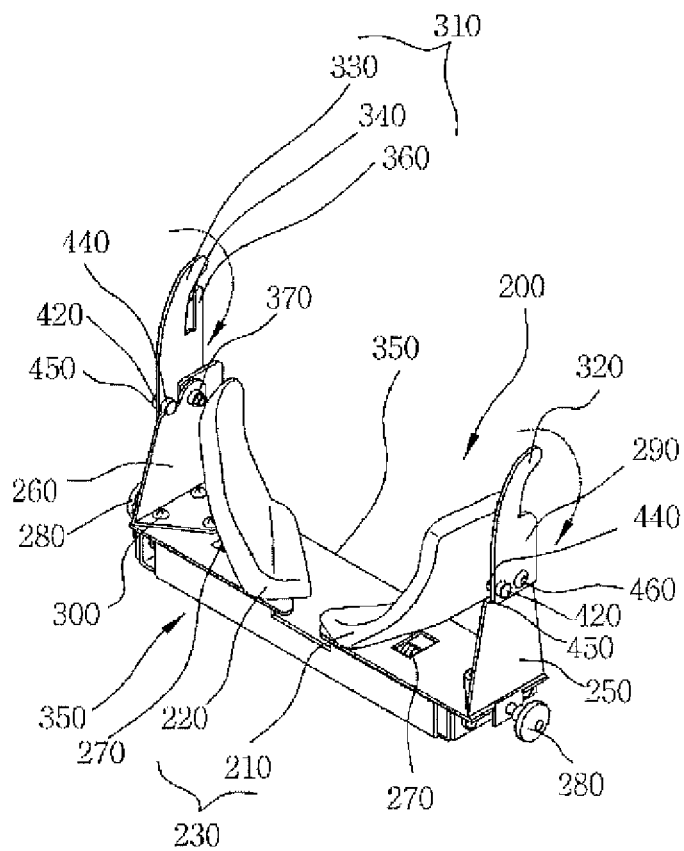
Figure 9:
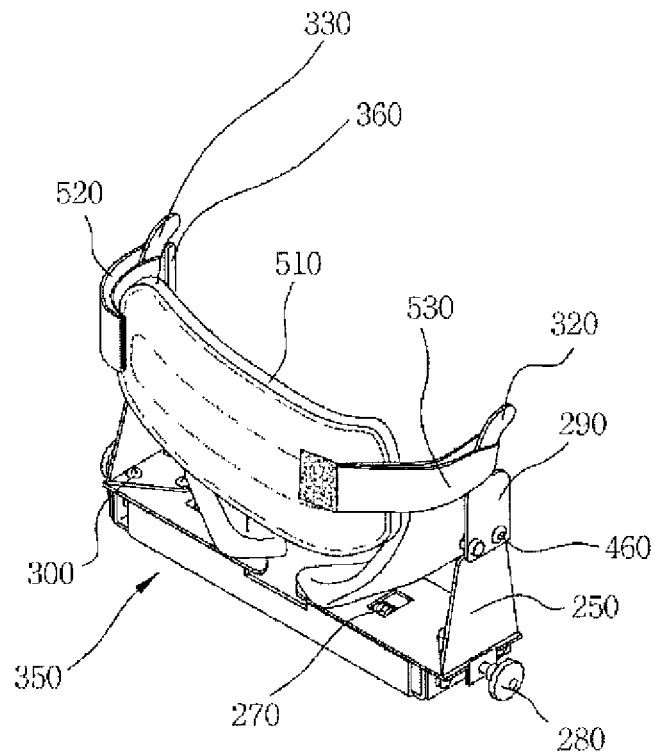

As shown in FIG. 7, rails 110 are respectively formed in the both sides of the support 100. The support 100 is formed to have a certain height, a top portion of the support is formed of a flat shape so as for the head supporting part 200, the upper body supporting part 240 and the lower body supporting part 400 to be disposed at the top portion, and a frame is formed inside the support 100 so as for the connecting means 500 and the pressure means 600 to be disposed.

The head support 200 of the head fastener for cervical traction for medicinal purposes according to the present invention, as shown in FIGS. 7 to 10, is disposed at the head portion of the support 100 so as to hold and support a head of a person receiving treatment. At this point, the head support 200 includes a neck fixing part 230 holding a neck through an upper portion which supports a head, is formed to open and close an upper part, and is opened.

An upper portion of the supporting part 200 with a cover such that a person receiving treatment lies comfortably.

The neck fixing part 230 is configured with a left support 210 and a right support 220 disposed at an upper portion of a control box 350 to support a neck. The left and right supports 210 and 220 are coupled to a gap control screw 270 to be formed, and can move in a left-and-right direction by rotating a gap control lever 280 connected to the gap control screw 270.

As described above, the left and right supports 210 and 220 are connected to the gap control screw 270 to move with the gap control screw 270 such that a gap can be controlled depending on a physical condition.

A left chin support 250 and a right chin support 260 formed to fix a chin are fixed to be coupled to the control box 350 with a fixing bolt 300 in a periphery of the neck fixing part 230.

A chin supporting pad fixing part is couple to an upper portion of the left and right chin supports 250 and 260 to fix a chin supporting pad 510.

The chin supporting pad fixing part is coupled to a left chin supporting pad fixing part 290 and a right chin supporting pad fixing part 310. The left chin supporting pad fixing part 290 is formed to be coupled to the left chin support 250 with a rotation shaft 460. Also, a through hole is formed in the left chin supporting pad fixing part 290, and a stop bolt 420 and a nut 440 are coupled to the through hole.

Next, the right chin supporting pad fixing part 310 is formed to be coupled to the right chin support 260 with a rotation shaft 370. Also, a through hole is formed in the right chin supporting pad fixing part 310, and a stop bolt 420 and a nut 440 are coupled to the through hole.

As described above, a stopper 450 is respectively formed in top surfaces of the left and right chin supports 250 and 260 such that the left chin supporting pad fixing part 290 and the right chin supporting pad fixing part 310 are coupled to the left and right chin supports 250 and 260 to rotate, and fix the chin supporting pad 510. Therefore, the stop bolt 420 of the left and right chin supporting pad fixing parts 290 and 310 is disposed at the stopper 450 such that the left and right chin supporting pad fixing parts 290 and 310 does not rotate any more.

A hanging string 520 is formed in one side of the chin supporting pad 510 and a control string 530 is formed in the other side of the chin supporting pad 510 such that the chin supporting pad 510 is coupled to the left and right chin supporting pad fixing parts 290 and 310. Also, a velcro tape is formed in the control string 530 so as to be attached after a control.

The hanging string 520 is inserted into a separation preventing groove 340 formed between a front protrusion 330 and a rear protrusion 360 of the right chin supporting pad fixing part 310 to be coupled. Also, the control string 530 including the velcro tape is hung on a protrusion 320 of the left chin supporting pad fixing part 290 to be controlled, attached and fixed.

Figure 10:
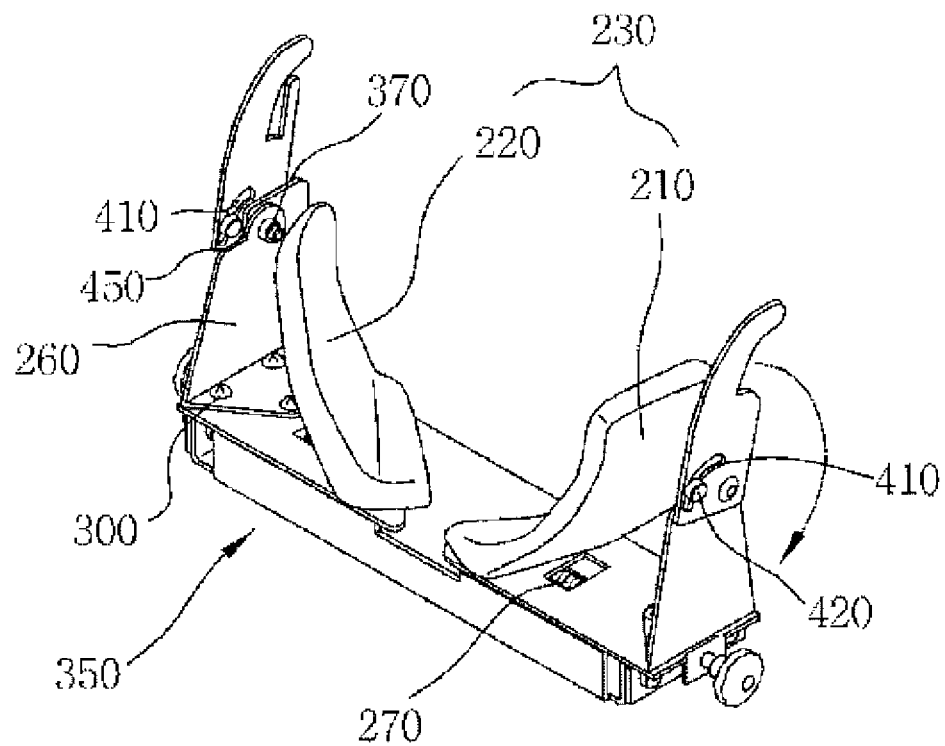

A rotation angle rail groove 410 is formed in another embodiment of the present invention shown in FIG. 10 such that a rotation angle of each of the left and right chin supporting pad fixing parts 290 and 310 can be controlled.

The rotation angle rail groove 410 is formed such that a position of the stop bolt 420 of each of the left and right chin supporting pad fixing parts 290 and 310 can be changed, and thus, a rotation angle of the left and right chin supporting pad fixing parts 290 and 310 can be changed.

The stop bolt 420 is coupled to the rotation angle rail groove 410 such that the left and right chin supporting pad fixing parts 290 and 310 do not rotate any more.

A stop washer and a special nut may be provided with the stop bolt 420 such that the stop bolt 420 is not pushed or is not moved when the stop bolt 420 is coupled to the rotation angle rail groove 410.

The present invention includes the left and right supports so as to stably fix a head, and includes the left and right chin supporting pad fixing parts formed in an upper portion so as to fix a chin. Moreover, the present invention is characterized in that the chin supporting pad is coupled to the left and right chin supporting pad fixing part so as to prevent a chin from being pulled.

The invention claimed is:

1. A pelvic fastener for lumbar traction of physical therapy device applied to a physical therapy device comprising a bed plate (2) disposed at an upper portion of a frame (1) such that the bed plate (2) moves backwards and forwards, and a pelvic bed (3) attached to an upper portion of the bed plate (2) to support lumbar vertebrae, the pelvic support structure comprising:

brackets (10) respectively connected by each of shafts (H1) to both front sides of the bed plate (2) rotatably in a left-and right direction;

pelvic supporters (20) respectively connected by each of shafts (H2) to upper portions of the brackets (10) rotatably in a left-and-right direction and having a curved shape to surround a pelvis;

pelvic cushions (30) respectively disposed at inner surfaces of the pelvic supporters (20) to come into tight contact with the pelvis; and female and male buckles (40 and 50) connected to upper portions of the pelvic supporters (20) and the pelvic cushions (30) by bands (41 and 51), the female and male buckles (40 and 50) being one-touch detachable buckles.

2. The pelvic fastener of claim 1, wherein, supporting boards (2a) are respectively disposed at both lower portions of a front side of the bed plate (2), a connecting piece (11) expanding to the supporting board (2a) is bent in a horizontal direction to be formed in a lower portion of the bracket (10), and a reinforcing piece (12) connected to the supporting board (2a) of the bed plate (2) rotatably in a left-and-right direction by the shaft (H3) is bent in a vertical direction to be formed in an end portion of the connecting piece (11).

3. The pelvic fastener of claim 1, wherein, a vertical long hole (21) having a slope inserting hole (21a) opening into the outside is formed in one side of a central portion of the pelvic supporter (20), horizontal long holes (22 and 23), each of which has a slope inserting hole (22a or 23a) opening into the outside, are respectively formed in an upper portion and a lower portion of the pelvic supporter (20), connecting parts (31 and 32), each of which is inserted into the vertical long hole (21) and the horizontal long hole (23) through the slope inserting holes (21a and 23a), are attached to the central portion and the lower portion of an outer surface of the pelvic cushion (30), a connecting part (41a) inserted into the horizontal long hole (22) through the slope inserting hole (22a) of the pelvic supporter (20) is formed in one end portion of the band (41), and one end portion of the band (51) is attached to outer side of the pelvic cushion (30) by using a sewing method.

4. The pelvic fastener of claim 1, wherein, the pelvic supporter (20) is formed of metal material.

* * * * *